United States Patent [19]

Kavka

[11] Patent Number: 5,756,745
[45] Date of Patent: May 26, 1998

[54] PREPARATION OF NALBUPHINE HAVING LOW LEVELS OF β-EPIMER

[75] Inventor: Frank Kavka, St. Louis, Mo.

[73] Assignee: Mallinckrodt Medical, Inc., St. Louis, Mo.

[21] Appl. No.: 737,887

[22] PCT Filed: May 16, 1995

[86] PCT No.: PCT/US95/06097

§ 371 Date: Nov. 26, 1996

§ 102(e) Date: Nov. 26, 1996

[87] PCT Pub. No.: WO95/32973

PCT Pub. Date: Dec. 7, 1995

Related U.S. Application Data

[63] Continuation of Ser. No. 251,460, May 31, 1994, abandoned.

[51] Int. Cl.⁶ ............................................... C07D 489/08
[52] U.S. Cl. ............................................................. 546/44
[58] Field of Search ................................... 546/44, 45

[56] References Cited

U.S. PATENT DOCUMENTS

| | | | |
|---|---|---|---|
| 3,332,950 | 7/1967 | Blumberg | 546/45 |
| 3,393,197 | 7/1968 | Pachter | 546/44 |
| 4,795,813 | 1/1989 | Schwartz | 546/44 |
| 5,112,975 | 5/1992 | Wallace | 546/45 |

OTHER PUBLICATIONS

L. Sargent et al., *J. Org. Chem.*, 23: pp. 1247–1251 (1958).
A. Currie et al., *J. Chem. Soc.*, pp. 773–781 (1960).
R. Olofson et al., *J. Org. Chem.*, 49: pp. 2081–2082 (1984).
A. Benarab et al., *Tetrahedron Letters*, 34, pp. 7567–7568 (1993).

*Primary Examiner*—Donald G. Daus
*Attorney, Agent, or Firm*—Jeffrey S. Boone; Linda Lewis

[57] ABSTRACT

A process is described for the synthesis of nalbuphine. The process results in a product having very low levels of the undesirable β-epimer. The process is a five-step synthesis that begins with a compound such as an $N,O^3$-bis (alkoxycarbonyl)-14-hydroxynormorphinone.

9 Claims, No Drawings

PREPARATION OF NALBUPHINE HAVING LOW LEVELS OF β-EPIMER

This is a 371 of PCT US 95/06097 filed 05/16/95 which is a con. of 08/251,460 filed 5/31/94, now abandoned.

Nalbuphine hydrochloride ($C_{21}H_{27}NO_4 \cdot HCl$; CAS Registry No.:23277-42-2; IUPAC name: (−)-17-(cyclobutylmethyl)-4,5α-epoxymorphinan-3,6 α, 14-triol hydrochloride) is a synthetic partial opiate agonist analgesic of the phenanthrene series. It is structurally related to naloxone and oxymorphone, but is pharmacologically similar to pentazocine and butorphanol. Nalbuphine hydrochloride is used as an analgesic in the treatment of moderate to severe pain such as that associated with acute and chronic medical disorders including cancer, orthopedic problems, renal or biliary colic, migraine or vascular headaches, and surgery. The drug is also used to provide preoperative sedation and analgesia and as a supplement to surgical anesthesia.

The synthesis of nalbuphine results in small quantities of the β-epimer (diastereoisomer) of nalbuphine. The difference is the orientation of the hydroxyl moiety at the 6-position. Little is known about the pharmacological activity of the β-epimer. In many countries, including the United States, regulatory authorities consider epimers of the desired compound to be impurities which must be minimized. The β-epimer of nalbuphine can be reduced to very low levels by recrystallization. However, such recrystallizations are very time consuming and expensive. Further, because nalbuphine recrystallizations have high losses, and many recrystallizations (e.g.: 5 or 6) are required to reach low levels of β-epimer, recrystallization results in unacceptably low yields.

The synthesis of nalbuphine hydrochloride is taught, for example, in U.S. Pat. No. 3,332,950 (Blumberg; Endo Laboratories; 1967). Blumberg teaches the $LiAlH_4$ reduction of N,$O^3$-bis(cyclobutylcarbonyl)noroxymorphone to nalbuphine (see columns 3 and 4). The process of this patent produces nalbuphine with a weight ratio of nalbuphine to β-epimer of about 6:1. Further processing yields slightly less than 10% β-epimer.

L. J. Sargent, et al., Hydroxylated Codeine Derivatives, J. Org. Chem., 23, 1247–1251 (1958), shows several reactions of codeine derivatives, in particular, the stereospecific sodium borohydride reduction of 14-hydroxycodeinone to 14-hydroxycodeine.

A. C. Currie, et al., Some reactions of 14-Hydroxycodeine, J. Chem. Soc., 773–781 (1960) is similar to Sargent, et. al.

R. A. Olofson, et al., A New Reagent for the Selective, High-Yield N-Dealkylation of Tertiary Amines: Improved Syntheses of Naltrexone and Nalbuphine, J. Org. Chem., 49, 2081–2082 (1984), teaches a novel reagent, α-chloroethyl chloroformate, for the demethylation of tertiary amines to yield secondary amines. This reference, in the final paragraph, shows the use of this chemistry to synthesize nalbuphine from 14-hydroxydihydrocodeinone.

A. Benarab, et al., Utilisation du Groupment Cyanométhyle comme Motif Protecteur des Phénols, Amines et Carbamates, Tetrahedron Letters, 34, No. 47, 7567–7568 (1993), teaches the use of the cyanomethyl unit as a protecting group for phenols, primary and secondary amines, and carbamates. Optimized conditions for formation and hydrolysis of cyanomethyl in the presence of the other hydrogenolysis sensitive groups such as O- and N- benzyl groups are presented.

SUMMARY OF THE INVENTION

Briefly, the invention is a process for the synthesis of nalbuphine. The process is particularly useful for the synthesis of nalbuphine having very low levels of the undesirable β-epimer.

DETAILED DESCRIPTION OF THE INVENTION

In this specification and claims, numerical values and ranges are not critical unless otherwise stated. That is, the numerical values and ranges may be read as if they were prefaced with the word "about" or "substantially".

Step 1: Reduction of N—$R^1$,$O^3$—$R^2$-14-hydroxynormorphinone

The process of the invention begins with an N—$R^1$,$O^3$—$R^2$- 14-hydroxynormorphinone,

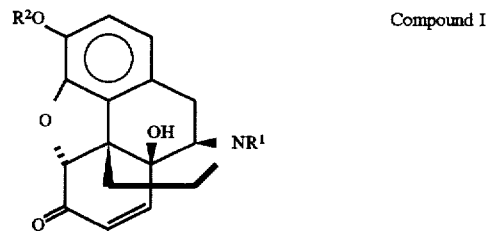

Compound I in which each of $R^1$ and $R^2$ is independently a protective group that may be removed by hydrolysis and/or hydrogenolysis. For instance, although not experimentally verified, and in any event not preferred, the protective groups of A. Benarab, et al., discussed above, may be suitable for use in the invention. Generally, $R^2$ may be any alkoxycarbonyl, aroxycarbonyl, or arylmethyl moiety, that will not interfere with the reactions and $R^1$ may be any alkoxycarbonyl or aroxycarbonyl moiety that will not interfere with the reactions. Generally, the alkoxycarbonyl group will have 1 to 12, desirably 1 to 8, more desirably 2 to 6, preferably 2 to 4, and most preferably 2 carbon atoms in the alkoxy portion. Suitable alkoxycarbonyl groups include propoxycarbonyl and ethoxycarbonyl. Generally, the aroxycarbonyl group will have 6 to 12, desirably 6 to 10, more desirably 6 to 8, preferably 6 or 7, and most preferably 6 carbon atoms in the aroxy portion. Suitable aroxycarbonyl groups include phenoxycarbonyl. Generally, the arylmethyl ether group will have 6 to 12, desirably 6 to 10, more desirably 6 to 8, preferably 6 or 7, and most preferably 6 carbon atoms in the aryl portion. Suitable arylmethyl ether groups include napthylmethyl ether and benzyl ether. The preferred genus is an N,$O^3$-bis(alkoxycarbonyl)-14-hydroxynormorphinone. The preferred species is N,$O^3$-bis (ethoxycarbonyl)-14-hydroxynormorphinone [$R^1=C_2H_5OC(O)$— and $R^2=C_2H_5OC(O)$—].

Since the $R^1$ and $R^2$ groups will ultimately be cleaved from the molecule, it is only important that they participate in the desired reactions. It will be apparent to those skilled in the art that many variations on these groups will be suitable in the practice of this invention. These compounds are available from the process described in U.S. Pat. No. 5,112,975 (Wallace; Mallinckrodt Chemical; 1992), incorporated herein by reference.

The N—$R^1$,$O^3$—$R^2$-14-hydroxynormorphinone is reduced using a reducing agent that is mild enough to not attack the double bond at the 7–8 position. The reducing agent is desirably an alkali metal borohydride, preferably sodium borohydride. Other suitable reducing agents are known to those skilled in the art (see, for example, J. March, Advanced Organic Chemistry, 4th Edition, 910–911; J Seyden-Penne, Reductions by the Alumino- and Borohydrides in Organic Synthesis, 7–8 and 89). The reaction preferably takes place in the presence of a solvent such as ethanol and can be either a one-phase reaction or a two phase reaction. A weak acid such as acetic acid is desired to buffer the system. The quantity of acid is important, too little acid may result in dimer formation and too much acid may inactivate the reducing agent. If glacial acetic acid is used, generally about 0.5 mole of acid will be used per mole of reactant.

The resulting product is an N—R$^1$,O$^3$—R$^2$-14-hydroxynormorphine.

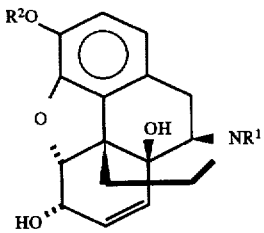

Compound II wherein R$^1$ and R$^2$ are as defined above. The product is desirably an N,O$^3$-bis(alkoxycarbonyl)-14-hydroxynormorphine, and preferably N,O$^3$-bis (ethoxycarbonyl)-14-hydroxynormorphine [R$^1$=C$_2$H$_5$OC (O)— and R$^2$=C$_2$H$_5$OC(O)—].

At this stage the β-epimer content is generally less than 4% and is typically about 2%. The later processing will lower the β-epimer amount, possibly due to solubility and/or crystal structure factors.

Step 2: Hydrogenation of N—R$^1$,O$^3$—R$^2$-14-hydroxynormorphine

The product of step one (preferably N,O$^3$-bis (ethoxycarbonyl)-14-hydroxynormorphine) is then hydrogenated with hydrogen gas and a hydrogenation catalyst such as a supported metal catalyst. 5% palladium on charcoal is an exemplary hydrogenation catalyst for this reaction. This reaction saturates the double bond at the 7–8 position and, in the instance of an O$^3$-arylmethyl compound, hydrogenolyses the arylmethyl ether to a free phenol. The resulting product is (except in the case of an O$^3$-arylmethyl starting compound), an N—R$^1$,O$^3$—R$^2$-α-noroxymorphol

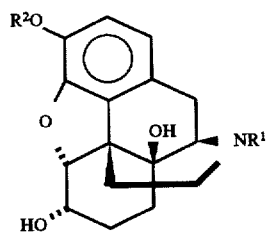

Compound III wherein R$^1$ and R$^2$ are as defined above. The product is preferably N,O$^3$-bis (ethoxycarbonyl) -α-noroxymorphol [R$^1$=C$_2$H$_5$OC(O)= and R$^2$=C$_2$H$_5$OC(O)—].

As mentioned above, in the instance of an O$^3$-arylmethyl compound, this reaction hydrogenolyses the arylmethyl ether to a free phenol. In this case the resulting product is an N—R$^1$-α-noroxymorphol

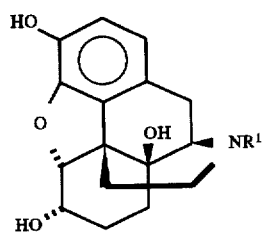

Compound III.B

Step 3: Hydrolysis of N—R$^1$,O$^3$—R$^2$-α-noroxymorphol
The N—R$^1$,O$^3$—R$^2$-α-noroxymorphol (preferably N,O$^3$-bis (ethoxycarbonyl)-α-noroxymorphol) [or N—R$^1$-α- noroxymorphol if an O$^3$ -arylmethyl compound was used in step 2], is hydrolyzed using a hydrolysis agent such as a strong acid (for instance hydrochloric acid, sulfuric acid, or methanesulfonic acid). sulfuric acid is an exemplary hydrolysing agent. The reaction preferably takes place in water. The resulting product is α-noroxymorphol.

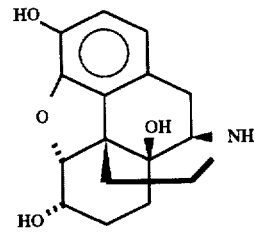

Compound IV

At this stage the β-epimer content is generally less than 3% and is typically about 1.5%. Later processing will continue to lower the β-epimer amount.

Step 4: Acylation of α-Noroxymorphol

The α-noroxymorphol is acylated with a conventional acylating agent such as cyclobutanecarbonyl chloride. The addition of triethylamine will scavenge the hydrochloric acid byproduct, causing it to be bound as triethylamine hydrochloride. If the HCl is not scavenged, it will react with the α-noroxymorphol, converting it to the hydrochloride, and thus substantially lowering the yield of the acylation reaction. The reaction preferably takes place in tetrahydrofuran (THF). Although the starting material, α-noroxymorphol, is not soluble in THF, the reaction products are. Furthermore, the triethylamine hydrochloride byproduct is not soluble in THF, making the separation quite simple. This reaction produces a mixture of N,O$^3$-bis (cyclobutylcarbonyl)-α-noroxyorphol

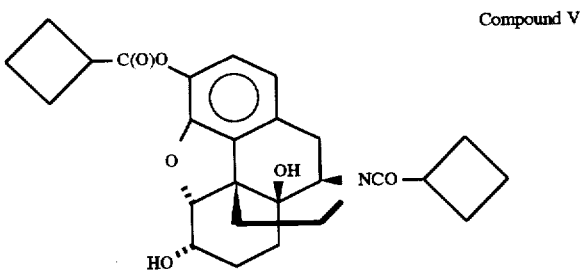

Compound V and N-cyclobutylcarbonyl-α-noroxymorphol.

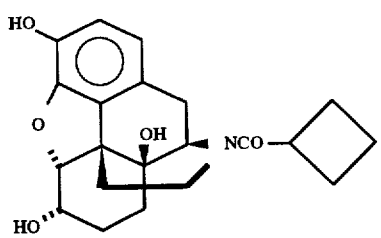

Compound VI

Step 5: Reduction of N,O$^3$-bis(cyclobutylcarbonyl)-α-Noroxymorphol and N-cyclobutylcarbonyl-α-noroxymorphol The N,O$^3$-bis(cyclobutylcarbonyl)-α-Noroxymorphol and N-cyclobutylcarbonyl-α-noroxymorphol are reduced using a reducing agent such as lithium aluminum hydride. Other suitable reducing agents are known to those skilled in the art (see, for example, J. March, Advanced Organic Chemistry, 4th Edition,1212–1213; H. House, Modern Synthetic Reactions, Second Edition (1972), 89; K. Niehues, Complex Hydrides as Reducing Agents in the organic Chemistry, III. Hydride Symposium (1979), 60; M. Fieser, et. al., Reagents for Organic Synthesis, Vol. 5, 596). The addition of ethyl acetate at the end of the reaction will quench the reducing agent. Citric acid can be added to bind with the aluminum from the lithium aluminum hydride. The resulting product is nalbuphine.

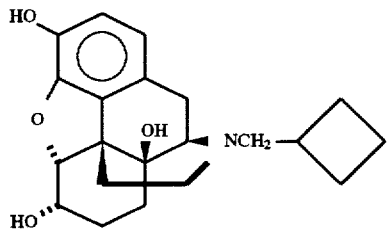

Compound VII

The nalbuphine can be converted to the hydrochloride salt (preferred for pharmaceutical use) by preparing a slurry with alcohol and hydrochloric acid, cooling, and filtering. The solid can then be recrystallized from water. These salt formation and purification steps are well known in the art.

At this stage the β-epimer content is generally less than 1.5, desirably less than 1.3, and preferably less than 1%, and is typically about 0.3 to 0.8%.

The invention will be further explained in the following examples. In the examples, all parts and percentages are by weight unless otherwise specified.

EXAMPLE 1
Compound I to Compound II (Single-Phase System)

8.6 g N,$O^3$-bis(ethoxycarbonyl)-14-hydroxynormorphinone (Compound I), 206 ml 2B (denatured) ethanol, and 0.57 ml glacial acetic acid were stirred to dissolve the solid at 29° C. The solution was cooled to 6° C. and 0.35 g sodium borohydride was added in portions with stirring and cooling within 14 minutes at 6°–7°. The mixture was stirred for 1 hour at 4°–6° C. and 0.28 ml glacial acetic acid was added. Then 2.7 ml acetone was added, the mixture was warmed up to room temperature and stirred for 15 minutes. The solvents were removed under reduced pressure and the residue was dissolved in a mixture of 100 ml ethyl acetate and 40 ml water. Ammonia was added to pH 6.5, the layers were separated, and the lower layer was extracted with ethyl acetate. The combined organic phases were dried with magnesium sulfate, the solvents were removed under reduced pressure, and the residue was crystallized with toluene to give 8.0 g N,$O^3$-bis(ethoxycarbonyl)-14-hydroxynormorphine (Compound II) of 97.0% purity by liquid chromatography.

EXAMPLE II
Compound I to Compound IV (Two-Phase System)

(Step 1) 141.7 g N,$O^3$-bis(ethoxycarbonyl)-14-hydroxynormorphinone (Compound I), 569 ml ethyl acetate, and 116 ml 2 B (denatured) ethanol were stirred at 28° C. to dissolve the solids. The solution was cooled to 20° C. and 4.6 ml glacial acetic acid, 2.12 g tetrabutylammonium bromide, and 106 ml water were added (for ease of addition, the tetrabutylammonium bromide can be dissolved in the water). The mixture was cooled to 6° C. and 6.27 g sodium borohydride was added in portions with vigorous stirring and cooling at 6°–9° C. within 35 minutes. The mixture was stirred for 1 hour at 5°–7° C. and 10.7 ml glacial acetic acid and 24.4 ml acetone were added. The mixture was stirred for 10 minutes and the layers were separated. The lower phase was extracted with 73 ml ethyl acetate. Compound II was determined to be present.

(Step 2) The combined upper layers were introduced to a hydrogenation vessel and flushed with nitrogen. A hydrogen atmosphere was introduced and Compound II was hydrogenated over 4.6 g 5% palladium on charcoal at 35 psi for 9 hours. The catalyst was filtered off and washed with ethanol. The combined filtrate and wash were concentrated. Compound III was determined to be present.

(Step 3) A mixture of 111 ml sulfuric acid and 399 ml water, and the reaction mixture was refluxed for 3.5 hours. At this point the reaction to Compound IV is complete and the remaining steps are for purification and separation. 10.4 ml Glacial acetic acid was added to the cool reaction mixture and pH was adjusted to 4.75 with ammonia at 50°–55° C. The mixture was diluted to 1.1 l with water, heated to 90° C., and treated with 7.1 g Darco G60 activated charcoal and 4.3 g of a filter aid. More ammonia was added to pH 9, the mixture was cooled to 5°–10° C., and α-noroxymorphol (Compound IV) was filtered off and washed with cold water. The yield was 86.9%, purity 93.9% by liquid chromatography. A second crop was obtained from mother liquors by adding ammonium sulfate, extracting with isopropyl alcohol, concentrating the organic extracts, isolating the hydrochloride, and precipitating the base of 95.0% purity in 5.9% yield. Peak area ratio α- vs. β-noroxymqrphol was 94.5:0.44 (0.47% β-epimer) in the first crop and 98.4:0.26 (0.26% β-epimer) in the second crop (these are not weight percentages).

EXAMPLE III
Compound IV to Compound VII (Step 4) Cyclobutanecarbonyl chloride (4.84 ml) was added dropwise to a stirred mixture of 7.23 g α- noroxymorphol (Compound IV), 6.94 ml triethylamine, and 65 ml tetrahydrofuran at 18°–23° C. within 69 minutes. The mixture was stirred for 30 minutes at 19°–22° C., filtered, and the solids were washed with tetrahydrofuran. The combined filtrate and wash were concentrated to about 55 ml. At this point Compounds V and VI were determined to be present.

(Step 5) The concentrate was added slowly to a solution of 82 mmoles lithium aluminum hydride in tetrahydrofuran. The mixture was refluxed for 3 hours and cooled down. Ethyl acetate (9.6 ml) was added dropwise with stirring and cooling. Then 10 ml 6M and 23.6 ml concentrated hydrochloric acid were added carefully with stirring and cooling. Citric acid monohydrate (24.0 g) was charge in, the mixture was stirred for several minutes and then alkalized to pH 8.85 first with 10 ml ammonia and then 24 ml 50% sodium hydroxide. The layers were separated, the lower phase was diluted with 10 ml water and extracted with 47 ml isopropyl alcohol. Both upper layers were combined, concentrated to 50 ml, the residue was acidified with 2 ml hydrochloric acid, and the remaining organic solvents were distilled off. The solids in the residue were dissolved by adding water and heating to 55°–60° C. at pH 2–3 and dilute ammonia was added to precipitate 7.8 g crude nalbuphine base, assaying for 93.2% nalbuphine (Compound VII) and 0.55% β-epimer.

What is claimed is:

1. A process for the production of nalbuphine comprising the steps of:
   (a) producing a-noroxymorphol by the hydrolysis of an N—$R^1$—,$O^3$—$R^2$ -a-noroxymorphol or an N—$R^1$-a-noroxymorphol wherein each of $R^1$ and $R^2$ is independently an alkoxy or aryloxy carbonyl protective group that can be removed by hydrolysis;
   (b) acylating the a-noroxymorphol to produce N,$O^3$-bis(cyclobutylcarbonyl)-a-noroxymorphol and/or N-cyclobutylcarbonyl-a-noroxymorphol; and
   (c) reducing the N,$O^3$-bis(cyclobutylcarbonyl)-a-noroxymorphol and/or N-cyclobutylcarbonyl-a- noroxymorphol with an alkali metal aluminum hydride to produce nalbuphine.

2. The process of claim 1 wherein the N—$R^1$,$O^3$—$R^2$-α-noroxymorphol or an N—$R^1$-α-noroxymorphol are produced by the hydrogenation of an N—$R^1$,$O^3$—$R^2$-14-hydroxynormorphine.

3. The process of claim 2 wherein the N—$R^1$,$O^3$—$R^2$-14-hydroxymorphine is produced by the reduction of an N—$R^1$,$O^3$—$R^2$-14-hydroxymorphinone with a metal borohydride.

4. The process of claim 1, 2 or 3 wherein $R^1$ is an alkoxycarbonyl group having 1 to 12 carbon atoms in the alkoxy portion or an aroxycarbonyl group having 6 to 12 carbon atoms in the aroxy portion; and $R^2$ is an alkoxycarbonyl group having 1 to 12 carbon atoms in the alkoxy portion, an aroxycarbonyl group having 6 to 12 carbon atoms in the aroxy portion or an arylmethyl ether group having 6 to 12 carbon atoms in the aryl portion.

5. The process of claim 4 wherein $R^1$ and $R^2$ are each independently alkoxycarbonyl groups having 2 to 6 carbon atoms in the alkoxy portion.

6. The process of claim 5 wherein $R^1$ and $R^2$ are each ethoxycarbonyl groups.

7. A process for the production of nalbuphine comprising the steps:
   A. stereospecifically reacting an N,$O^3$-bis(alkoxycarbonyl)-14-hydroxynormorphinone with a metal borohydride to produce an N,$O^3$-bis(alkoxycarbonyl)-14-hydroxynormorphine;
   B. hydrogenating the N,$O^3$-bis(alkoxycarbonyl)-14-hydroxynormorphine to produce an N,$O^3$-bis(alkoxycarbonyl)-a-noroxymorphol;
   C. hydrolyzing the N,$O^3$-bis(alkoxycarbonyl)-a-noroxymorphol to produce a-noroxymorphol;
   D. acylating the a-noroxymorphol to produce N,$O^3$-bis(cyclobutylcarbonyl)-a-noroxymorphol and N-cyclobutylcarbonyl-a-noroxymorphol; and
   E. reducing the N,$O^3$-bis(cyclobutylcarbonyl)-a-noroxymorphol and N-cyclobutylcarbonyl-a-noroxymorphol with an alkali metal aluminum hydride to produce nalbuphine.

8. The process of claim 7 wherein the alkoxycarbonyl moieties are ethoxycarbonyl moieties.

9. A process for the production of nalbuphine having a b-epimer content of less than 1%, comprising:
   (a) reducing an N—$R^1$,$O^3$—$R^2$-14-hydroxynormorphinone with a metal borohydride, wherein each of $R^1$ and $R^2$ is independently an alkoxy or aryloxy carbonyl protective group that may be removed by hydrolysis, to produce an N—$R^1$,$O^3$—$R^2$-14-hydroxynormorphine having a b-epimer content of less than 4%; and
   (b) converting the N—$R^1$,$O^3$—$R^2$-14-hydroxynormorphine having a b-epimer content of less than 4% to nalbuphine having a b-epimer content of less than 1%.

* * * * *